US011450237B2

(12) United States Patent
Grant et al.

(10) Patent No.: US 11,450,237 B2
(45) Date of Patent: Sep. 20, 2022

(54) DYNAMIC INJECTION OF MEDICAL TRAINING SCENARIOS BASED ON PATIENT SIMILARITY COHORT IDENTIFICATION

(71) Applicant: International Business Machines Corporation, Armonk, NY (US)

(72) Inventors: Robert H. Grant, Atlanta, GA (US); Maruthi P. Koiloth, Little Elm, TX (US); Daniel Ruiz, Austin, TX (US); Zachary Silverstein, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 784 days.

(21) Appl. No.: 16/286,927

(22) Filed: Feb. 27, 2019

(65) Prior Publication Data
US 2020/0273372 A1   Aug. 27, 2020

(51) Int. Cl.
G09B 23/28 (2006.01)
A61B 34/10 (2016.01)
(Continued)

(52) U.S. Cl.
CPC ............ G09B 23/285 (2013.01); A61B 34/10 (2016.02); G09B 23/30 (2013.01);
(Continued)

(58) Field of Classification Search
CPC ................................ G09B 23/28; G09B 23/30
See application file for complete search history.

(56) References Cited

U.S. PATENT DOCUMENTS 5,396,886 A * 3/1995 Cuypers .............. A61B 5/0205
600/301
7,121,832 B2 10/2006 Hsieh et al.
(Continued)

FOREIGN PATENT DOCUMENTS

EP   2996105 A1   3/2016
WO   2016/040376 A1   3/2016

OTHER PUBLICATIONS

Appendix P, "List of IBM Patents or Patent Applications Treated as Related", Mar. 18, 2020, 2 pages.
(Continued)

*Primary Examiner* — Kurt Fernstrom
(74) *Attorney, Agent, or Firm* — Maeve M. Carpenter; Hunter E. Webb; Keohane & D'Alessandro, PLLC (57) ABSTRACT

Disclosed embodiments provide a computer-implemented technique for selection and/or modification of surgical simulation scenarios based on patient similarity cohort identification. Prior to undergoing surgery, medical information of a patient, including genomic, physiological, and/or environmental data, is used to identify a patient cohort. The patient cohort represents a statistically significant sample size of similar patients, and complications that may have arose during similar surgical procedures to the procedure planned for the patient. Relevant scenarios are identified based on the patient cohort. These scenarios are then input to a surgical simulation system. The surgical simulation system may be implemented by virtual reality, augmented reality, and/or physical workpieces used for surgical practice and training. This can increase the probability of a successful outcome for the patient, and furthermore save costs by reducing the risk of malpractice lawsuits, thereby potentially lowering overall healthcare costs.

10 Claims, 7 Drawing Sheets

(51) Int. Cl.
  *G09B 23/30* (2006.01)
  *G06N 20/00* (2019.01)
  *G16H 10/60* (2018.01)
(52) U.S. Cl.
  CPC ........ *A61B 2034/101* (2016.02); *G06N 20/00* (2019.01); *G06T 2210/41* (2013.01); *G16H 10/60* (2018.01)

(56) References Cited

U.S. PATENT DOCUMENTS

| | | | | |
|---|---|---|---|---|
| 7,653,556 | B2* | 1/2010 | Rovinelli | G09B 7/02 705/2 |
| 9,886,873 | B2* | 2/2018 | Patrickson | G09B 23/30 |
| 2008/0085499 | A1* | 4/2008 | Horvath | G09B 23/285 434/262 |
| 2009/0263775 | A1 | 10/2009 | Ullrich | |
| 2010/0153146 | A1* | 6/2010 | Angell | G06Q 40/08 705/7.28 |
| 2010/0153147 | A1* | 6/2010 | Angell | G06Q 10/04 705/7.28 |
| 2010/0167249 | A1 | 7/2010 | Ryan | |
| 2011/0165542 | A1* | 7/2011 | Campbell | G09B 7/00 434/219 |
| 2013/0189663 | A1 | 7/2013 | Tuchschmid et al. | |
| 2016/0242673 | A1* | 8/2016 | Grychtol | A61B 5/6831 |
| 2018/0344919 | A1* | 12/2018 | Jones | G16H 50/50 |
| 2019/0088356 | A1* | 3/2019 | Oliver | G16H 40/20 |

OTHER PUBLICATIONS

Fabrizio Cutolo et al., "A new head-mounted display-based augmented reality system in neurosurgical oncology: a study on phantom", Computer Assisted Surgery, 2017, vol. 22, No. 1, 16 pages.
Gabriele Wurm et al., "Cerebrovascular Biomodeling for Aneurysm Surgery: Simulation-Based Training by Means of Rapid Prototyping Technologies", Surgical Innovation, vol. 18, No. 3, pp. 294-306.
Neil Vaughan et al., "A Review of Virtual Reality Based Training Simulators for Orthopaedic Surgery", Medical Engineering & Physics, vol. 38, No. 2, 2016, 21 pages.
Willem I. M. Willaert et al., "Recent Advancements in Medical Simulation: Patient-Specific Virtual Reality Simulation", World Journal of Surgery, 2012, vol. 36, pp. 1703-1712.
Wieslaw L. Nowinski et al., "Simulation of Interventional Neuroradiology Procedures", Proceedings International Workshop on Medical Imaging and Augmented Reality, Shatin, Hong Kong, China, 2001, pp. 87-94.
Ka-Chun Siu et al., "Adaptive Virtual Reality Training to Optimize Military Medical Skills Acquisition and Retention", Military Medicine, vol. 181, 2016, pp. 214-220.
Ausra Mongirdiene et al., "The coagulation system changes in patients with chronic heart failure", Medicina (Kuanas), 2010, vol. 46, No. 9, pp. 642-647.
Fernstrom, Kurt, U.S. Appl. No. 16/522,812, Office Action, P201808012US02, dated Dec. 2, 2021, 18 Pgs.
Fernstrom, Kurt, U.S. Appl. No. 16/522,812, Notice of Allowance, P201808012US02, dated Jun. 21, 2022, 15 Pgs.
Fernstrom, Kurt, U.S. Appl. No. 16/522,812, Final Office Action, P201808012US02, dated Mar. 24, 2022, 16 Pgs.

* cited by examiner

DYNAMIC INJECTION OF MEDICAL TRAINING SCENARIOS BASED ON PATIENT SIMILARITY COHORT IDENTIFICATION

FIELD

The present invention relates generally to simulation of medical procedures and, more particularly, to dynamic injection of medical training scenarios based on patient similarity cohort identification.

BACKGROUND

Medical procedures are often complex and risky, even when everything goes as planned. When unexpected situations occur during a medical procedure, quick thinking is often necessary in order to save the patient. The training of healthcare professionals to review the team-based communication, problem-solving, and skills-based action necessary during such a stressful situation is vital to successful patient outcomes. Medical training simulation systems are useful tools for practicing medical procedures. They allow multiple practice sessions and enable physicians, nurses, and other medical staff the opportunity to prepare for and rehearse unexpected situations, such as heart failure during an operation.

Medical simulation systems can include computer-based simulation, where the user operates "virtual" tools on a "virtual" patient rendered on a computer screen, similar to a video game. Additionally, some medical simulation systems can include virtual reality, or augmented reality, for a more immersive experience. Furthermore, some medical simulation systems involve a physical element, such as a manikin or workpiece to allow practice of surgical procedures on a physical sample. In some cases, workpieces may include a portion of a human body (e.g., a leg, foot, etc.), and may be fabricated by 3D printing processes.

A recent study indicates that the cost of medical malpractice in the United States is in excess of $50 billion a year. Furthermore, due to medical error, it is estimated that as many as 400,000 patients die each year in the United States alone. Medical simulation has the potential to reduce medical errors and the associated costs, while improving the probability of successful outcomes in healthcare.

SUMMARY

In one embodiment, there is provided a computer-implemented method, comprising: receiving a medical information record for a patient; receiving a procedure request for a patient; identifying a cohort for the patient based on the medical information record; identifying a cohort risk factor that is related to the procedure request based on the identified cohort; determining a probability of occurrence for the cohort risk factor; and altering a surgical simulation corresponding to the procedure request in response to a probability of occurrence exceeding a predetermined threshold.

In another embodiment, there is provided an electronic computation device comprising: a processor; a memory coupled to the processor, the memory containing instructions, that when executed by the processor, perform the process of: receiving a medical information record for a patient; receiving a procedure request for a patient; identifying a cohort for the patient based on the medical information record; identifying a cohort risk factor that is related to the procedure request based on the identified cohort; determining a probability of occurrence for the cohort risk factor; and altering a surgical simulation corresponding to the procedure request in response to a probability of occurrence exceeding a predetermined threshold.

In yet another embodiment, there is provided a computer program product for an electronic computation device comprising: a computer readable storage medium having program instructions embodied therewith, the program instructions executable by a processor to cause the electronic computation device to perform the process of: receiving a medical information record for a patient; receiving a procedure request for a patient; identifying a cohort for the patient based on the medical information record; identifying a cohort risk factor that is related to the procedure request based on the identified cohort; determining a probability of occurrence for the cohort risk factor; and altering a surgical simulation corresponding to the procedure request in response to a probability of occurrence exceeding a predetermined threshold.

BRIEF DESCRIPTION OF THE DRAWINGS

Features of the disclosed embodiments will be more readily understood from the following detailed description of the various aspects of the invention taken in conjunction with the accompanying drawings.

The drawings are not necessarily to scale. The drawings are merely representations, not necessarily intended to portray specific parameters of the invention. The drawings are intended to depict only example embodiments of the invention, and therefore should not be considered as limiting in scope. In the drawings, like numbering may represent like elements. Furthermore, certain elements in some of the Figures may be omitted, or illustrated not-to-scale, for illustrative clarity.

DETAILED DESCRIPTION

Disclosed embodiments provide a computer-implemented technique for selection and/or modification of surgical simulation scenarios based on patient similarity cohort identification. In embodiments, a patient agrees (opts in) to share personal medical information, including genomic, physiological, and/or environmental data, that is used to identify a patient cohort. The patient cohort represents a statistically significant sample size of similar patients, and complications that may have arose during similar surgical procedures to the procedure planned for the patient. Relevant scenarios are identified based on the patient cohort. These scenarios may then be input to a surgical simulation system prior to a planned surgery. The surgical simulation system may be implemented by virtual reality, augmented reality, and/or physical workpieces used for surgical practice and training.

This can serve to better prepare surgeons, nurses, and/or other medical staff for unexpected situations that can occur during surgery. By practicing for these serious situations, the medical team is prepared to provide a faster and more successful response. This can increase the probability of a successful outcome for the patient, and furthermore, save costs by reducing the risk of malpractice lawsuits, thereby potentially lowering overall healthcare costs.

Figure 1:
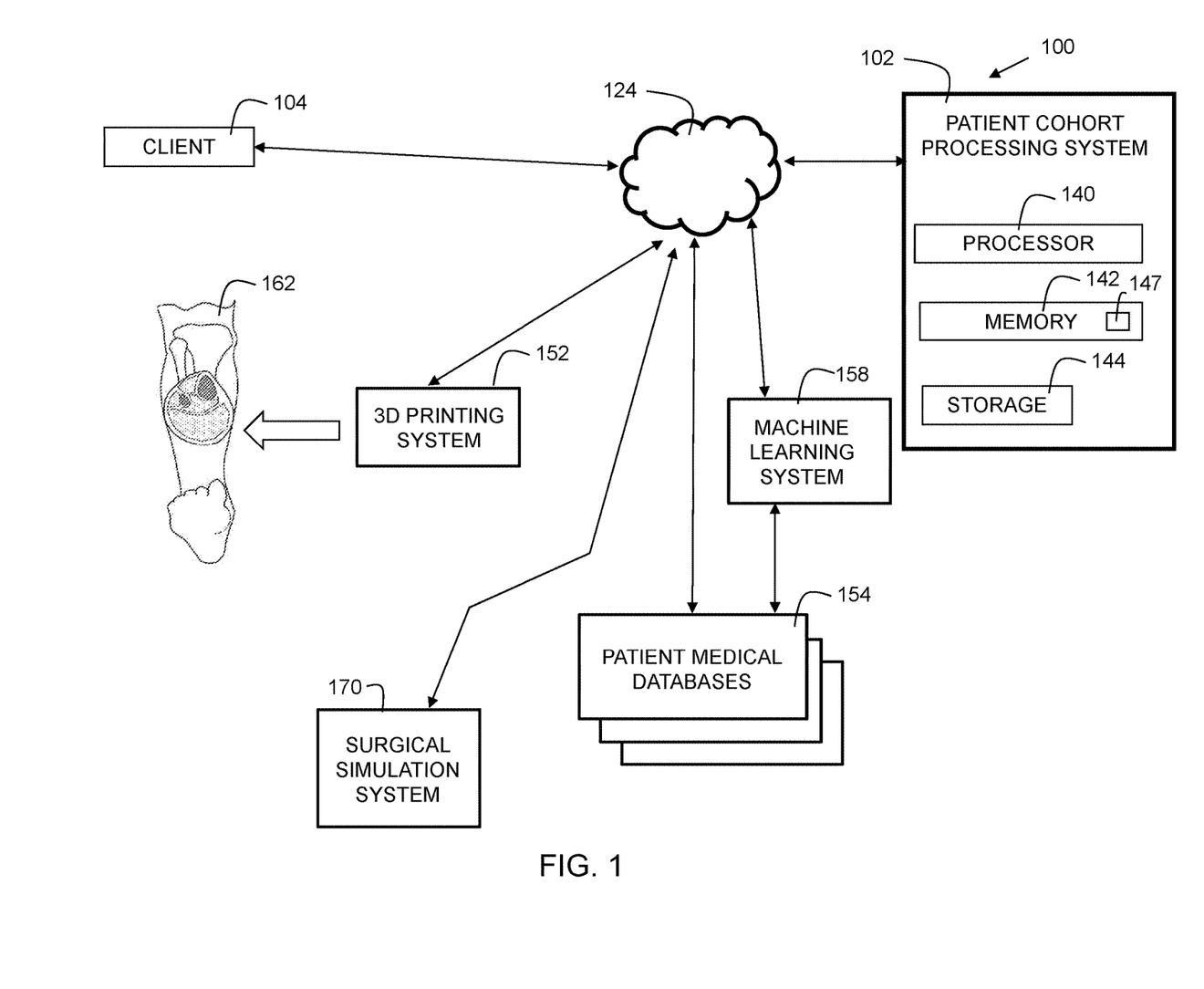
FIG. 1 shows an environment for embodiments of the present invention.

FIG. 1 is an environment 100 for embodiments of the present invention. Patient cohort processing system 102 comprises a processor 140, a memory 142 coupled to the processor 140, and storage 144. System 102 is an electronic computation device. The memory 142, contains instructions 147, that when executed by the processor 140, perform embodiments of the present invention. Memory 142 may include dynamic random-access memory (DRAM), static random-access memory (SRAM), magnetic storage, and/or a read only memory such as flash, EEPROM, optical storage, or other suitable memory. In some embodiments, the memory 142 may not be a transitory signal per se. In some embodiments, storage 144 may include one or more magnetic storage devices such as hard disk drives (HDDs). Storage 144 may additionally include one or more solid state drives (SSDs). System 102 is connected to network 124, which is the Internet, a wide area network, a local area network, or other suitable network.

Patient medical databases 154 are computer-accessible databases that may include patient data. The patient data can include information from electronic medical records. The patient data may include, for each patient, genotypic information, phenotypic information, environmental information, and information on previous medical procedures, including the outcome of the procedure, and a list of complications arising from the procedure and/or occurring during the procedure. The patient medical databases 154 may be stored in a SQL (Structured Query Language) format such as MySQL, a NoSQL format, such as MongoDB, or other suitable storage format now known or hereafter developed.

Machine learning system 158 may be used to analyze the data contained in the patient medical databases 154 to determine risk factors for a procedure. The machine learning system 158 may include regression algorithms, classification algorithms, clustering techniques, anomaly detection techniques, neural networks, Bayesian filtering, and/or other suitable techniques to analyze the patient medical databases 154.

In embodiments, risk factors are identified based on a patient cohort. As an example, a patient of a particular age group, background, and/or gender may be prone to certain complications during a medical procedure. The machine learning system 158 can identify a patient cohort from the patient medical databases 154. The patient cohort includes patient entries within the patient medical databases 154 that have a certain amount of similarity to a specific patient candidate. For the purposes of this disclosure, a patient candidate is a person for whom a medical procedure is planned. Continuing the example, if the patient candidate is a male, aged 60 years, and diabetic, then the patient cohort may include men ranging in age from 55 years to 65 years that are diabetic. The patient cohort may be further refined to men that have undergone a medical procedure similar or identical to the planned procedure for the patient candidate. Continuing the example, if a hip replacement surgery is planned for the patient candidate, then the patient cohort may be further refined to men ranging in age from 55 years to 65 years that are diabetic and have undergone a hip replacement surgery. The patient cohort may then be analyzed by the machine learning system to identify anomalies that occurred during/after the surgery. Continuing the example, it may be identified that heart failure occurred during the hip replacement surgery in 4 percent of the patients. In this case, heart failure is identified as a risk factor if the occurrence exceeds a predetermined threshold (e.g., 1 percent). For other patient cohorts, heart failure may not be a significant risk factor. Continuing the example, for a patient cohort of women aged 35-45 years that are non-diabetic, the heart failure risk during a hip replacement may be less than 1 percent. Thus, when preparing for hip replacement surgery on a patient candidate in the cohort of women aged 35-45 years that are non-diabetic, it may not be advisable to spend time practicing a heart failure scenario since other risk factors may take priority. In contrast, when preparing for hip replacement surgery on a patient candidate in the cohort of men ranging in age from 55 years to 65 years that are diabetic, it would be advisable to spend time practicing a heart failure scenario, since the probability of such an occurrence during hip replacement surgery is elevated, as compared with other patient cohorts.

The identified risk factors are communicated from the patient cohort processing system 102 to the surgical simulation system 170. The surgical simulation system 170 can include, but is not limited to, a computer-based simulation, where users perform procedures on a rendered human body on a computer display. The surgical simulation system 170 can include, but is not limited to, a virtual reality simulation, where a user wears virtual reality goggles that render a simulation of a medical procedure. The surgical simulation system 170 can include, but is not limited to, a physical simulation, where a user practices on a physical workpiece such as a manikin or portion of a human body. The physical workpiece may be comprised of plastic. In some embodiments, the physical workpiece may be built by 3D printing techniques. In some embodiments, the physical workpiece may include silicone "skin" or other silicone components. In some embodiments, the physical workpiece includes tubes and pumps for fluid transport within the physical workpiece to simulate blood flowing through veins, urine flow, and/or other fluid flow. The surgical simulation system 170 can include, but is not limited to, an augmented reality simulation. In these embodiments, a user may wear augmented reality goggles that display information, guidance, and/or training feedback to the user while the user is practicing on a physical workpiece. The physical workpiece may be built by any suitable technique, and made from any suitable materials.

In embodiments, the surgical simulation system 170 receives risk factors from patient cohort processing system 102 and, in response to receiving the risk factors, the surgical simulation system incorporates the risk factors into a simulation of a planned procedure for the patient candidate. Referring again to the example of a hip replacement procedure for a man of age 60 years who is also diabetic, a surgeon can practice the procedure on a surgical simulation system 170 in advance of performing the actual surgery. To better prepare the surgeon, unexpected scenarios such as heart failure can be injected into the simulation, based on risk factors associated with the patient cohort corresponding to the patient candidate. In this way, the surgeon rehearses scenarios that have been known to previously occur in similar patients, thereby becoming better prepared to handle those situations during a real medical procedure.

Embodiments can further include 3D printing system 152. The 3D printing system 152 may include a Stereolithography (SLA) system, Fused deposition Modeling (FDM) system, Selective Laser Sintering (SLS) system, Selective Laser Melting (SLM) system, Electronic Beam Melting (EBM) system, Laminated Object Manufacturing (LOM) system, Binder Jetting (BJ) system, and/or other suitable 3D printing system now known or hereafter developed. 3D printing system 152 can be used to make a customized workpiece 162 for practicing during a medical simulation practice session. In embodiments, the 3D printing system 152 is programmed to build a workpiece 162 containing certain characteristics. As an example, in preparation for leg surgery, the 3D printing system may be programmed with parameters pertaining to characteristics of a leg belonging to a specific patient cohort. Example parameters could include, but are not limited to, bone density, bone diameter, cartilage placement, vein placement, vein strength, muscle size, and tendon size. One or more of these aforementioned parameters may be used in customization of a 3D printed workpiece 162. As an example, if a patient cohort indicates tendons that are smaller than average, then the 3D printing system may modify the printing of the tendons accordingly, so that they are smaller than average. In this way, a surgeon practicing on the workpiece encounters a scenario that may better reflect the conditions of the patient candidate.

Client device 104 is connected to network 124. Client device 104 is a user computing device, such as a tablet computer, laptop computer, desktop computer, smartphone, PDA, or other suitable device that can communicate over a computer network. The client device 104 may be used to provide patient candidate information to the patient cohort processing system 102. The patient candidate information can include, but is not limited to, age, gender, ethnicity, weight, height, medical history, medical procedure to be performed, heredity information, genetic information, and/ or other suitable information. The patient cohort processing system 102 orchestrates the machine learning system 158 to identify a patient cohort from the patient medical databases 154, identifies relevant risk factors, and then alters the scenario of the surgical simulation system and/or 3D printing system 152 accordingly. Although one client device is shown, in implementations, more client devices can be in communication with the system 152 shown over the network 124.

Figure 2:
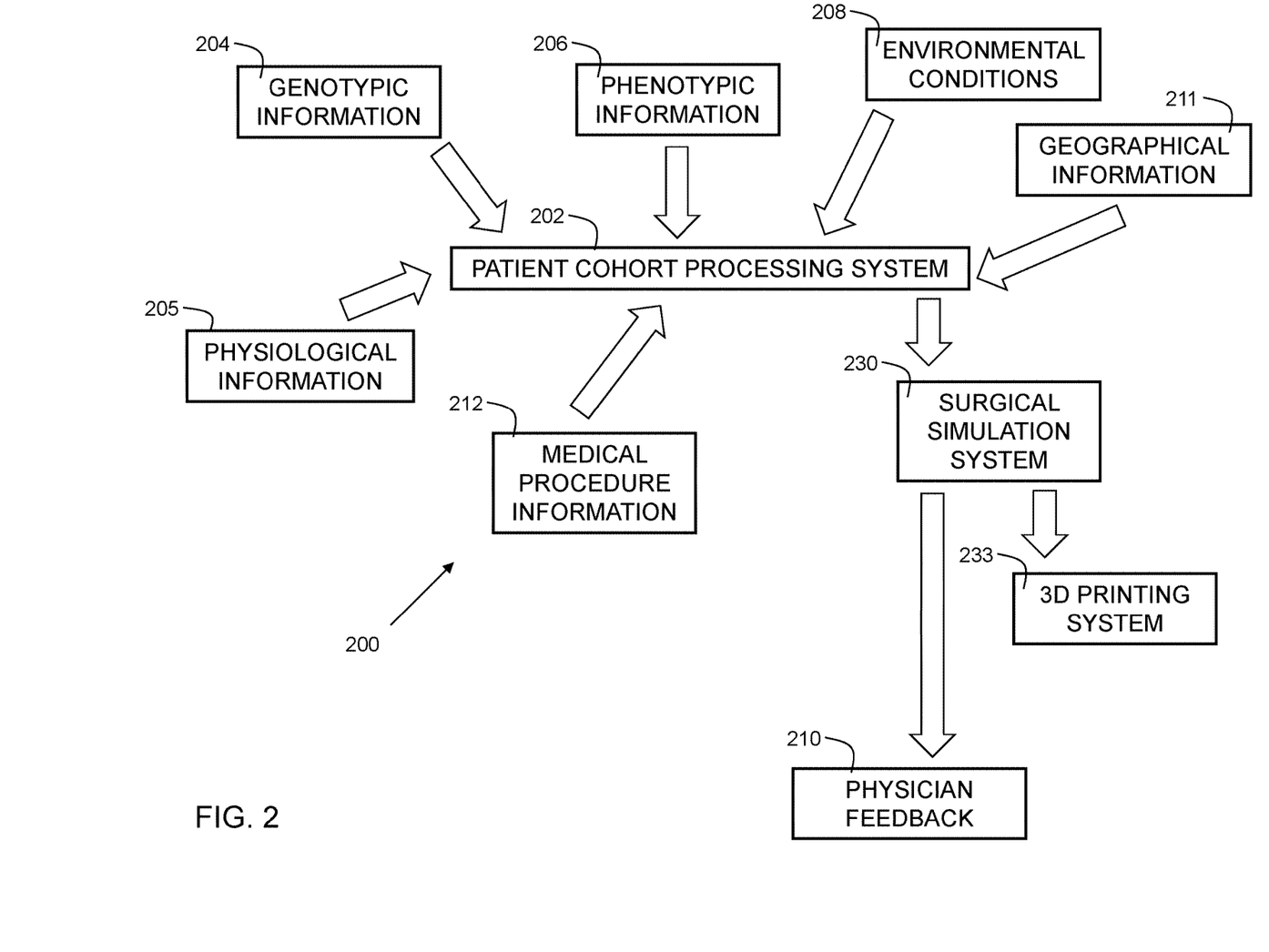
FIG. 2 shows a block diagram of elements of embodiments of the present invention.

FIG. 2 shows a block diagram 200 of elements of embodiments of the present invention. The block diagram 200 illustrates information flow. The patient cohort processing system 202 receives a variety of inputs to custom-tailor the medical training (surgical) simulation for a specific patient candidate, and procedure that is to be performed on that patient candidate.

In embodiments, the input information can include genotypic information 204. The genotypic information can include sets of genes and/or alleles within the DNA of a patient candidate that is responsible for particular traits. In embodiments, the input information can include physiological information 205. The physiological information can include, but is not limited to, blood type, blood sugar levels, blood pressure, heart rate, resting respiration rate, body temperature, and/or cholesterol levels. In embodiments, the input information can include phenotypic information 206. The phenotypic information can include observable information such as height, weight, skin tone, hair color, etc.

In embodiments, the input information can include environmental conditions 208. The environmental conditions can include, for example, occupation information. For instance, carpet installers, roofers, and other types of occupations require prolonged periods of knee bending, or putting pressure on the knees. As such, people with these types of occupations may have certain risk factors that are applicable to certain medical procedures (such as knee surgery). In embodiments, the environmental conditions are used to alter the training scenario provided by the surgical simulation system 230 to better reflect the conditions of the patient candidate. Embodiments can include receiving a medical information record for a patient. This can include electronic medical records.

Embodiments can further include receiving a procedure request for a patient. This can include alphanumeric codes pertaining to a surgical procedure (e.g., hip replacement). Embodiments can further include identifying a cohort for the patient based on the medical information record. As an example, if the patient candidate is a male that is 60 years of age and diabetic, then the patient cohort may include men with ages ranging from 55 years to 60 years that are diabetic and have undergone hip replacement surgery.

Embodiments can further include identifying one or more cohort risks factor that are related to the procedure request. As an example, if a high percentage of patients in the patient cohort experienced blood clots during the hip replacement surgery, then blood clots is identified as a cohort risk factor. Embodiments can further include determining a probability of occurrence for the cohort risk factor. This determination may be made based on the number of occurrences within the cohort. Embodiments can further include, in response to a probability of occurrence exceeding a predetermined threshold, altering a surgical simulation corresponding to the procedure request. This can include injecting a blood clot occurrence into a hip replacement surgical simulation scenario.

In embodiments, the input information can include geographical information 211. In embodiments, identifying a cohort comprises performing a geographic correlation technique. The geographic correlation technique can include identifying a risk factor that is abnormally high in people living in a certain area. For example, if a particular town's water supply is contaminated with lead, then the people living in that town may have certain risk factors during surgery that people living in a town with a clean water supply. In embodiments, these geographic specific risk factors are identified and used to alter the training scenario provided by the surgical simulation system 230 to better reflect the conditions of the patient candidate.

The patient cohort processing system 202 receives medical procedure information 212. The medical procedure information 212 describes the type of medical procedure the patient candidate is expected to undergo, and for which a surgeon desires to practice prior to the actual procedure being performed. In embodiments, the medical procedure information can be conveyed using CPT (Current Procedural Terminology) codes, HCPCS (Healthcare Common Procedure Coding System) codes, CDT (Code on Dental Procedures and Nomenclature) codes, and/or other suitable technique for conveyance of procedure information.

In embodiments, the identified patient cohort risk factor (s) are filtered against the medical procedure information 212. As an example, if the patient cohort risk information includes risk factors specific to knee surgery, then those risk factors are relevant if the patient candidate is undergoing knee surgery, but may not be relevant if the patient candidate is undergoing a dental procedure. Thus, in the case of a dental procedure, risk factors specific to knee surgery may be ignored. Other situations may not rise to the level of critical emergency, but can still be simulated. As an example, a percentage of the human population has "flipped organs" in which case, an organ such as a kidney may not be oriented in the typical manner, but instead is positioned in a reverse orientation. The surgical simulation system 230 can be programmed to generate a flipped organ training scenario to help prepare a surgical team for that condition should it arise in a patient candidate.

The patient cohort processing system 202 uses the relevant risk factors to program specific scenarios and/or probabilities into the surgical simulation system 230. In some embodiments, these risk factors can be used to alter parameters of the 3D printing system 233 that is fabricating a workpiece. Additionally, the surgical simulation system 230 may provide physician feedback 210, which may include a score (e.g. numerical score) indicative of how well the physician handled an unexpected emergency during the surgical simulation. This enables the physicians, surgeons, nurses, and other medical staff to compare simulation performances and track their progress in preparing for performing a specific medical procedure on a patient candidate.

Figure 3:
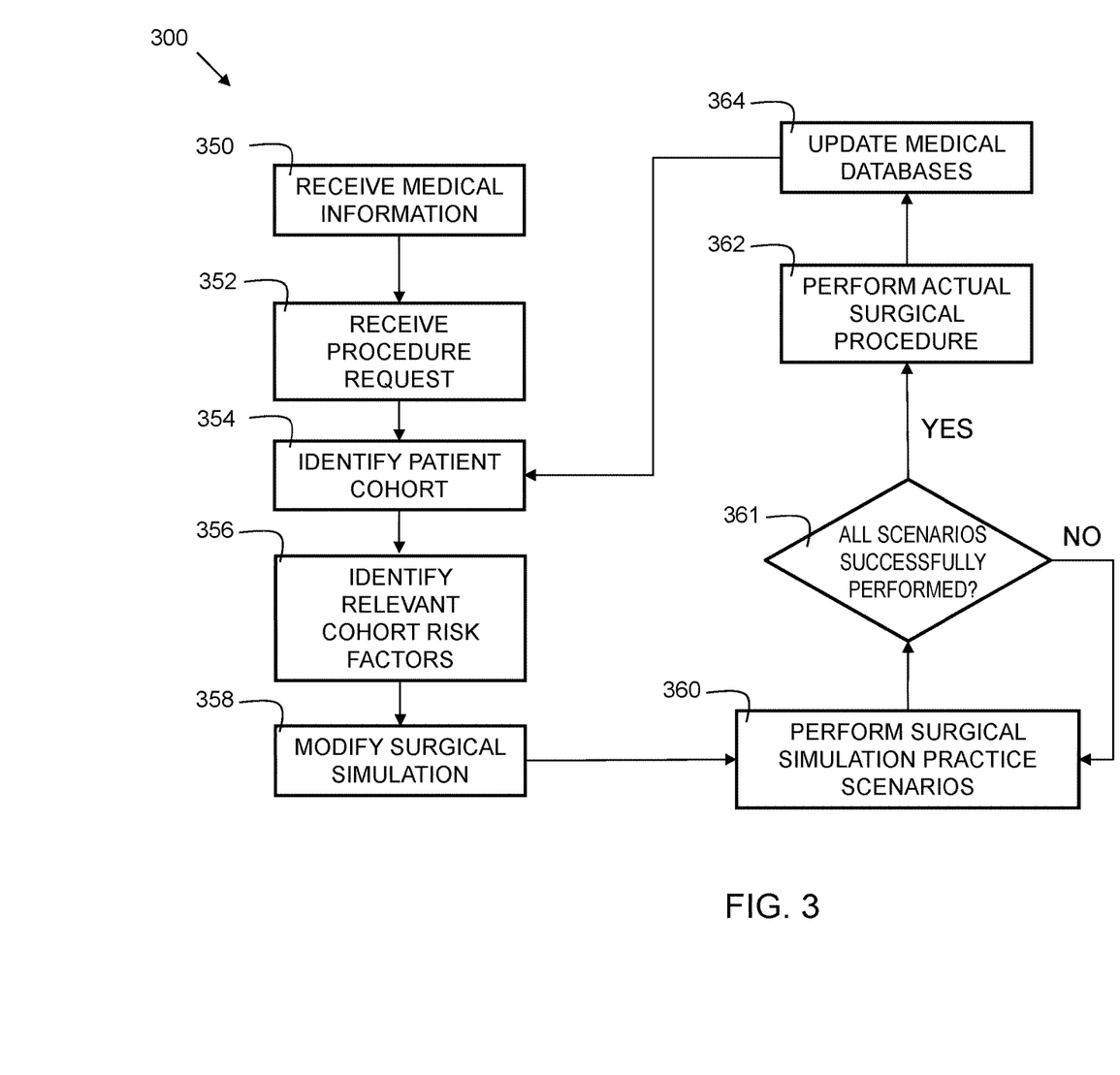
FIG. 3 is a flowchart indicating process steps for embodiments of the present invention.

FIG. 3 is a flowchart 300 indicating process steps for embodiments of the present invention. In process step 350 medical information from the patient candidate is received via an opt-in process in which the patient agrees to the release of such information. This information can include electronic medical records, physiological data (such as height, weight, blood pressure, cholesterol, blood type, blood sugar, heart rate, and the like), genetic information, heredity information, environmental information, occupational information, and/or other pertinent information. In embodiments, receiving a medical information record comprises receiving genotypic information. In embodiments, receiving a medical information record comprises receiving physiological information. In process step 352, a procedure request is received. This includes information regarding the type of medical procedure (e.g. surgery) that the patient candidate is scheduled to receive. In process step 354, a patient cohort is identified. This can include analyzing patent medical databases, crowdsourced information, and/or other sources of medical data to identify a patient cohort corresponding to the patient candidate. In embodiments, identifying a cohort comprises utilizing a Random Forest process. Random Forest is a supervised learning algorithm that can be used for both classification and regression problems. Other decision tree algorithms and/or other machine learning techniques, including, but not limited to, convolutional neural networks (CNN) may also be used instead of, or in addition to, the Random Forest process.

In process step 356, the relevant cohort risk factors are identified. These are risk factors that are applicable to the procedure received in process step 352. For example, if there is a cohort risk factor specific to back surgery, and the patient candidate is scheduled for back surgery, then the risk factor is relevant. Conversely, if there is a cohort risk factor specific to back surgery, and the patient candidate is scheduled for oral surgery, then that risk factor may not be relevant, and thus not included in surgical simulation. In embodiments, each cohort risk factor may be represented as a database record that includes metadata fields indicating relevant procedure types, parts of the body, and/or other factors to describe areas of relevance.

In process step 358, the surgical simulation is modified to incorporate relevant risk factors. Some risk factors may be generic, and relevant to all surgical procedures. By modifying the surgical simulation scenario based on patient cohort risk factors, where the patient cohort is based on the patient candidate, the surgical simulation includes scenarios that a physician may encounter while performing the real procedure, thus providing the medical team the opportunity to practice for such situations.

In process step 360, a surgical simulation scenario is performed. This can include performing a virtual reality based medical simulation, an augmented reality based simulation, and/or utilization of a physical model such as a 3D printed workpiece. In process step 361, a check is made to determine if all identified surgical scenarios have been successfully performed. In some embodiments, multiple surgical scenarios may be identified based on a patient cohort. As an example, a particular patient cohort may identify a first cohort risk factor of heart failure, and a second cohort risk factor of kidney failure. In such a case, there may be two practice scenarios; one for practicing heart failure during a surgical procedure, and another for practicing kidney failure during a surgical procedure. The measure of a successful performance may include, but is not limited to, the time required for the medical professional to complete the simulation scenario, the proper order of steps performed in the procedure, and/or other suitable factors.

Until all scenarios have been successfully performed, the process returns to step 360. When all scenarios are successfully performed, the process proceeds to step 362, where an actual surgical procedure is performed on a patient. In process step 364, the outcome of the actual surgery is updated into patient medical databases (154). The outcome may include information such as recovery times, complications that occurred during and/or after the surgery, patient survival, and/or other suitable information. In embodiments, the medical information is anonymized, removing personal identifiers such as names and birthdates, to preserve patient privacy. The updated medical databases are then used for future patient cohort identification at 354, as the process may repeat, continuing to refine and improve the accuracy of data for identifying relevant practice scenarios for surgical simulation.

Figure 4:
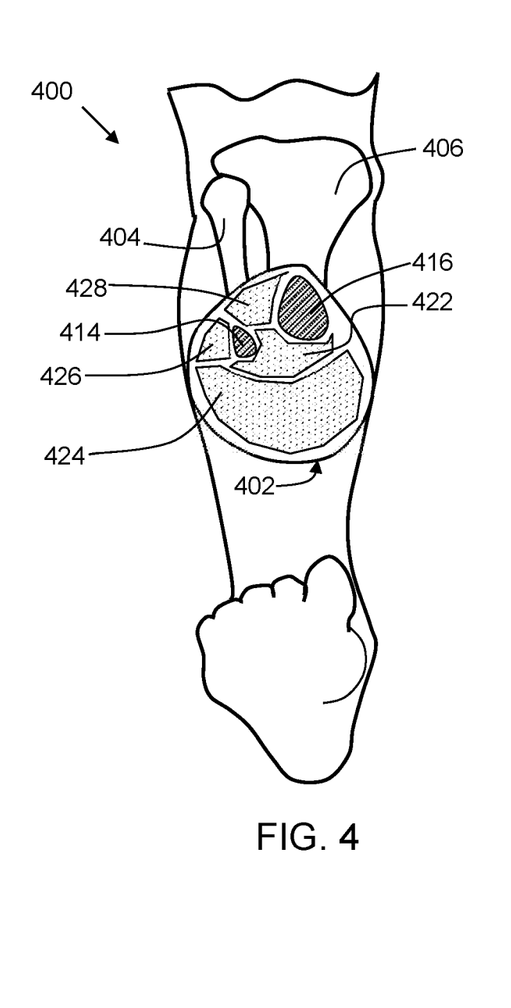
FIG. 4 shows an exemplary physical surgical simulation workpiece in accordance with embodiments of the present invention.

FIG. 4 shows an exemplary physical surgical simulation workpiece 400 in accordance with embodiments of the present invention. Workpiece 400 is a 3D printed model of a human leg. Reference number 402 shows a cross-section view of the leg. Tibia 406 has cross-section 416. Fibula 404 has cross section 414. Also visible in cross-section 402 is anterior compartment 428, first posterior compartment 422, second posterior compartment 424, and lateral compartment 426.

Compartment syndrome develops when swelling or bleeding occurs within a compartment. This can cause increased pressure on the capillaries, nerves, and muscles within the compartment. The result is that blood flow to muscle and nerve cells is disrupted. Without a steady supply of oxygen and nutrients, nerve and muscle cells can be damaged. In acute compartment syndrome, unless the pressure is relieved quickly, permanent disability and tissue death may result. The workpiece 400 may comprise a 3D printed model that renders compartments of different sizes, differing amounts of muscle within the compartments, and/or other factors that can lead to compartment syndrome.

Compartment syndrome most frequently occurs in the anterior compartment of the lower leg (calf). It can also occur in other compartments in the leg, as well as in the arms, hands, feet, and buttocks. Surgical treatment can include an operation that is designed to expand the compartments so that there is more room for the muscles to swell. This is something that can be practiced using a simulation on a 3D printed workpiece in accordance with embodiments of the present invention.

As an example use case of an embodiment of the present invention, a doctor is notified of a patient candidate with a fractured leg. The patient cohort similarity identification determines that about ten percent of the patient cohort have compartment syndrome. The doctor can then practice the leg surgery on a 3D printed leg that is fabricated based on the patient candidate data. Thus, the patient cohort processing system modifies the training scenario for repairing the fractured leg to include compartment syndrome. The patient candidate's health readings and the simulation data rendered by the surgical simulation system show an increase in pressure as one would expect to see with compartment syndrome. During the training scenario, the doctor interacts with the workpiece 400 and also responds to surgical simulator indications via augmented reality goggles or other suitable electronic device. The surgical simulation training scenario covers the proper protocol and treatment method for repairing a patient candidate with a fractured leg and compartment syndrome, instead of just a fractured leg, thereby providing an improved training experience that may better reflect real-world situations. In embodiments, altering the surgical simulation comprises controlling a 3D printing process. In embodiments, controlling the 3D printing process includes printing a leg model that includes compartment syndrome characteristics.

Figure 5:
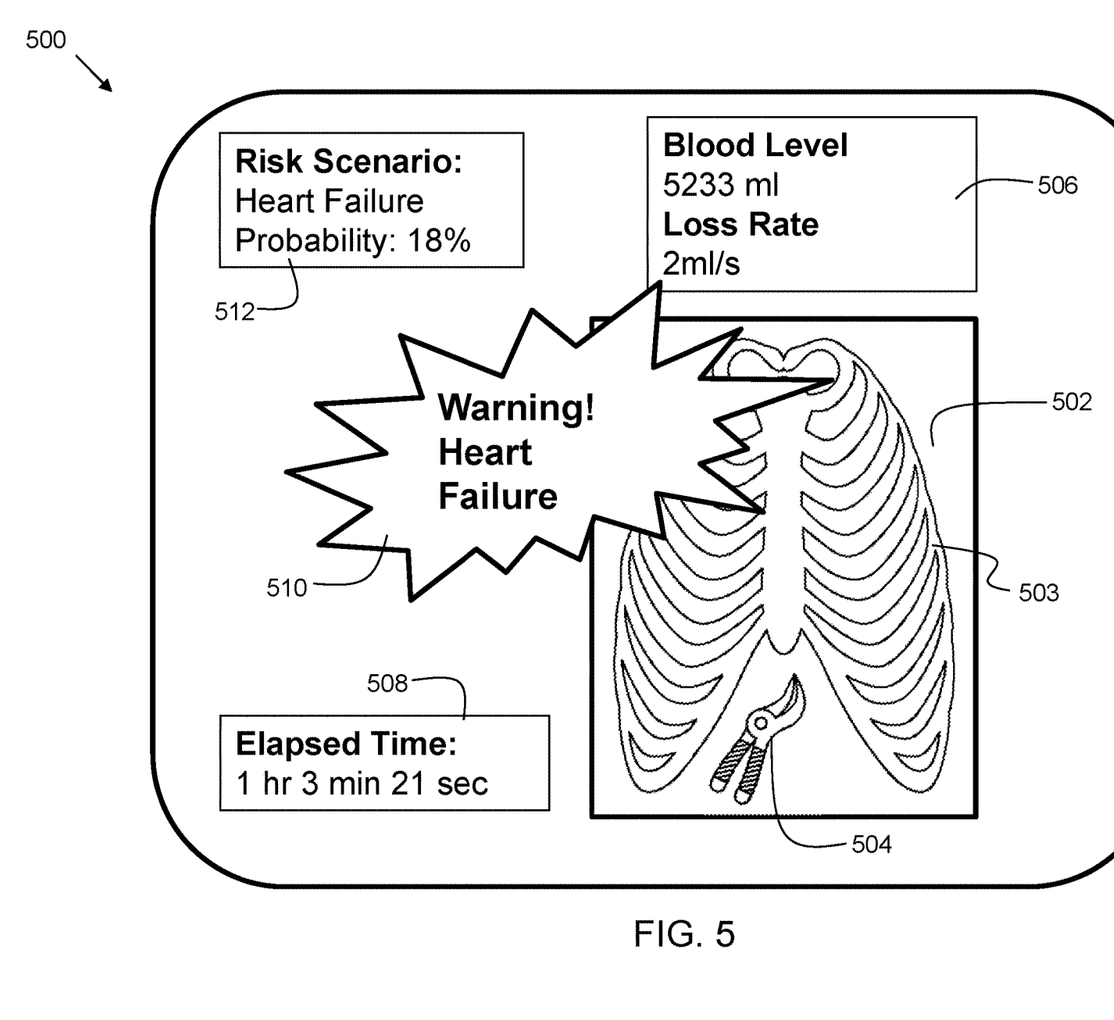
FIG. 5 shows an exemplary virtual surgical simulation in accordance with embodiments of the present invention.

FIG. 5 shows an exemplary virtual surgical simulation 500 in accordance with embodiments of the present invention. The virtual surgical simulation may be rendered on an electronic display such as that of a tablet computer, laptop computer, desktop computer, or other suitable electronic computing device. The simulation 500 includes a virtual operating area 502 of a patient. In this example, the virtual operating area 502 shows a human rib cage 503. The simulation 500 may further include a virtual surgical tool 504. During the simulation scenario, a user manipulates the virtual surgical tool 504 via a mouse, trackball, gestures, or other suitable device or method. While one tool is shown in simulation 500, in practice there may be multiple types of tools that a user can select and use as part of the simulation. Data field 506 shows virtual patient information, including blood level and loss rate. Data field 508 shows an elapsed time. Data field 512 indicates a risk scenario that is provided to the surgical simulation by the patient cohort processing system 102. Data field 510 indicates a risk factor condition that is currently occurring within the simulation. In the example of FIG. 5, the risk factor condition is heart failure. As the simulated heart failure occurs, the user practices stabilizing the virtual patient, administering treatment procedures and/or medications to treat the virtual patient. This causes the user to review the steps for handling an unexpected heart failure, so that when the doctor encounters such a scenario during a real operation, he/she can more readily recall the required treatment steps, increasing the chance of saving the patient.

As an example, Zach is a patient candidate who has a medical history of issues with blood coagulation. Through patient cohort identification, it is determined that there is an elevated risk of coagulation issues with increased heart failure. Zach's surgeon, Daniel, is practicing for an operation on him. Daniel uses client device 104 to provide the patient cohort processing system 102 with Zach's personal medical history. The patient cohort processing system 102 identifies a relevant patient cohort for Zach based on global medical statistics from patient medical databases 154. The processing of this information outputs risk factors that could affect Zach's surgery. As Daniel is practicing surgery with his computerized, virtual reality, augmented reality equipment and/or 3D printed simulation, the simulation dynamically changes to inject scenarios related to the risk factors. In this way, Daniel receives additional practice for scenarios that could happen to his patient. The surgical simulation system 170 injects a heart failure scenario into Daniel's practice surgery based on Zach's blood coagulation history and problems identified from Zach's patient cohort. Daniel has to take remediation activities in the simulation to stop Zach's simulated avatar from going into heart failure (e.g., as shown in FIG. 5). Daniel learns how to deal with that scenario in the course of surgery if it were to come up. As Daniel becomes better trained for some of these complications, he will be better prepared if they occur during the actual surgery.

Figure 6:
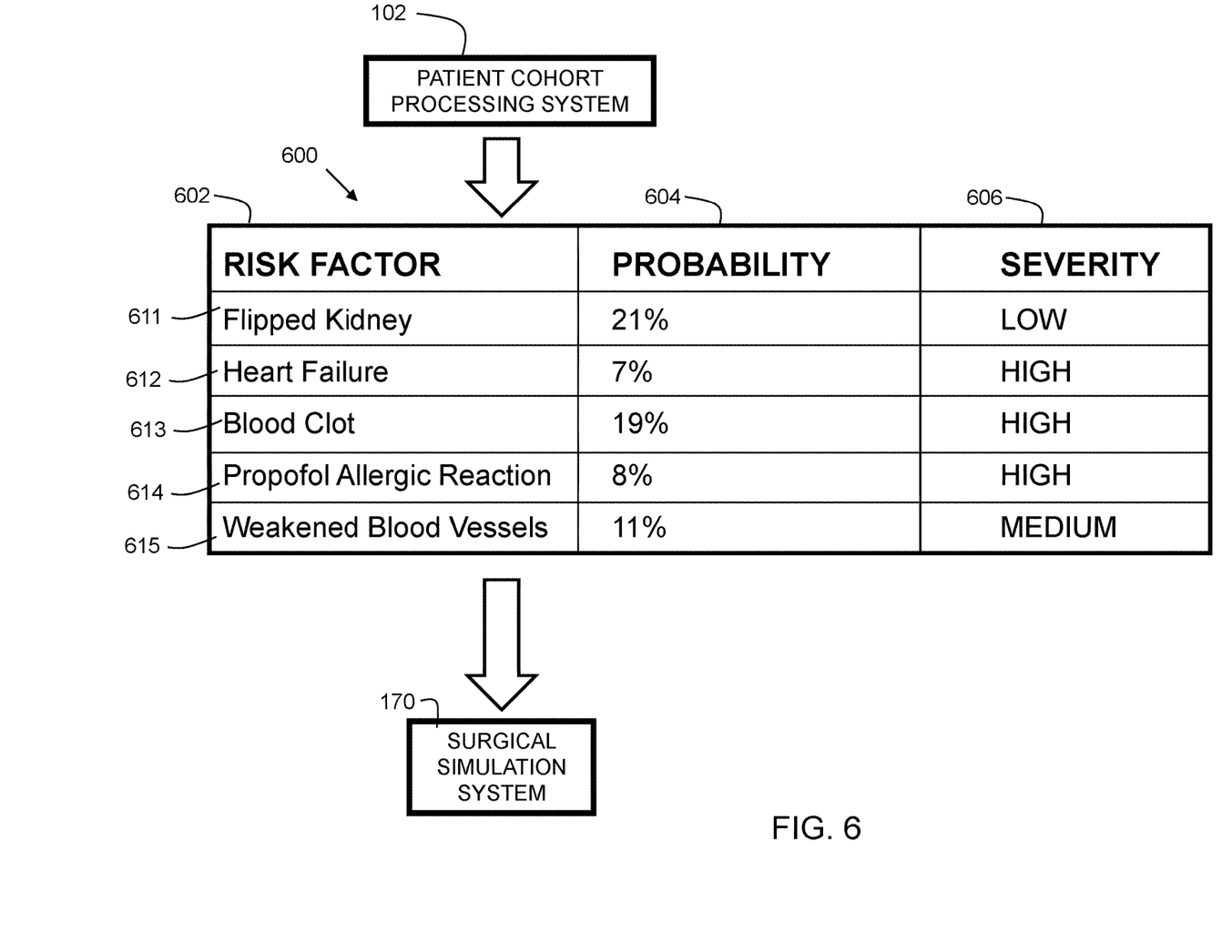
FIG. 6 shows an example data structure used in accordance with embodiments of the present invention.

FIG. 6 shows an example of a data structure 600 used in accordance with embodiments of the present invention. The patient cohort processing system 102 sends data structure 600 to the surgical simulation system 170 to set up training scenarios. Referring now to data structure 600 in more detail, column 602 shows a risk factor. Column 604 shows a probability for the corresponding risk factor in column 602. Column 606 shows a severity for the corresponding risk factor in column 602.

Row 611 shows data for a risk factor of a flipped kidney, having a probability of 21 percent and low severity. Row 612 shows data for a risk factor of heart failure, having a probability of 7 percent and high severity. Row 613 shows data for a risk factor of a blood clot, having a probability of 19 percent and high severity. Row 614 shows data for a risk factor of propofol allergic reaction, having a probability of 8 percent and high severity. Row 615 shows data for a risk factor of weakened blood vessels, having a probability of 11 percent and medium severity.

In embodiments, altering the surgical simulation comprises requesting an organ failure scenario. The organ failure can include, but is not limited to, heart failure, liver failure, and/or kidney failure. In embodiments, altering the surgical simulation comprises requesting an allergic reaction scenario. This can include an allergic reaction to latex, medications, airborne allergens, anesthesia, and/or other stimuli. The surgical simulation system 170 receives the data structure 600 and accordingly alters simulation scenarios based on the probability and/or severity of the risk factor. In some embodiments, the determination to include a risk factor may use the following "OR" filter logic:

IF (SEVERITY==HIGH) OR (PROBABILITY>X) THEN
   INCLUDE RISK FACTOR
ELSE
   DO NOT INCLUDE RISK FACTOR Thus, with the above filter logic, and X having a value of 15, then the risk factor in row 611 is included since the probability is 21 percent in column 604. The risk factors in rows 612, 613, and 614 are included since the severity in column 606 is high. The risk factor in row 615 is not included since the severity in column 606 is not high, and the probability in column 604 is below 15 percent. In embodiments, filter logic is used to remove one or more identified risk factors from the simulation scenarios. The aforementioned data structure 600 and filter logic are exemplary, and other fields, data structures, and/or filter logic processes are possible in embodiments of the present invention. In some embodiments, the patient cohort processing system 102 performs the evaluation with the filter logic, identifies suitable risk factors, and sends the suitable risk factors to the surgical simulation system 170. Other embodiments may utilize the following "AND" filter logic:

```
IF (SEVERITY == HIGH) AND (PROBABILITY > X) THEN
    INCLUDE RISK FACTOR
ELSE
    DO NOT INCLUDE RISK FACTOR
```

In this embodiment, only if the probability exceeds a predetermined threshold and the severity is high, is the risk factor included. Thus, embodiments may include determining a severity for the cohort risk factor; and altering a surgical simulation corresponding to the procedure request in response to a severity exceeding a predetermined level. This filter logic may provide a reduced set of medical scenarios as for simulation as compared with the "OR" filter logic. The "AND" filter logic may be suitable in cases where there is limited time for simulation scenarios. As an example, in cases where emergency surgery needs to be performed within a few hours, there may not be time to practice all available scenarios. In such a situation, the "AND" filter logic may be used to further filter the list of scenarios to be practiced. The aforementioned filter logic is exemplary, and other embodiments may utilize alternative and/or additional filters.

In another example, Bob is a patient candidate scheduled for some low risk shoulder surgery, and he has asthma on his medical record. Based on processing of a corresponding patient cohort that includes patients who suffer from asthma, it is determined that similar patients with asthma tend to have a higher anesthesia allergy occurrence rate which causes bronchospasm. As Joan is training on a simulation for Bob, the patient cohort processing system retrieves the patient candidate's (Bob's) relevant medical history and injects an allergic reaction scenario into the simulation. Joan then has to modify her practice/training simulation to deal with a bronchospasm issue. Because the simulation corresponding to Bob injects this scenario into the surgical simulation system 230, Joan is more aware of what to do in the situation and can train for this possible occurrence. When Bob has surgery, on the high relative chance that Bob does experience this allergic reaction, Joan is therefore able to rehearse various emergency scenarios prior to performing the actual surgery on Bob.

In yet another example, an oral surgeon needs to prepare for a major jaw surgery. The surgical simulation system 3D prints a patient candidate's jaw structure. Based on a corresponding patient cohort, it is determined that similar patients tend to have a specific nerve placed on the top mandible as compared with the bottom mandible, where the nerve is typically located. The surgeon does not know the patient has this condition, so they will have to be able to deal with the occurrence at time of working on a workpiece of a 3D printed jaw. When the jaw is printed, due to a high relative occurrence rate of this condition, it has this nerve printed on the top mandible instead of the bottom mandible. This gives the oral surgeon an opportunity to prepare for the unusual nerve placement situation in advance of the actual oral surgery.

Reference throughout this specification to "one embodiment," "an embodiment," "some embodiments", or similar language means that a particular feature, structure, or characteristic described in connection with the embodiment is included in at least one embodiment of the present invention. Thus, appearances of the phrases "in one embodiment," "in an embodiment," "in some embodiments", and similar language throughout this specification may, but do not necessarily, all refer to the same embodiment.

Moreover, the described features, structures, or characteristics of the invention may be combined in any suitable manner in one or more embodiments. It will be apparent to those skilled in the art that various modifications and variations can be made to the present invention without departing from the spirit and scope and purpose of the invention. Thus, it is intended that the present invention cover the modifications and variations of this invention provided they come within the scope of the appended claims and their equivalents. Reference will now be made in detail to the preferred embodiments of the invention.

Figure 7:
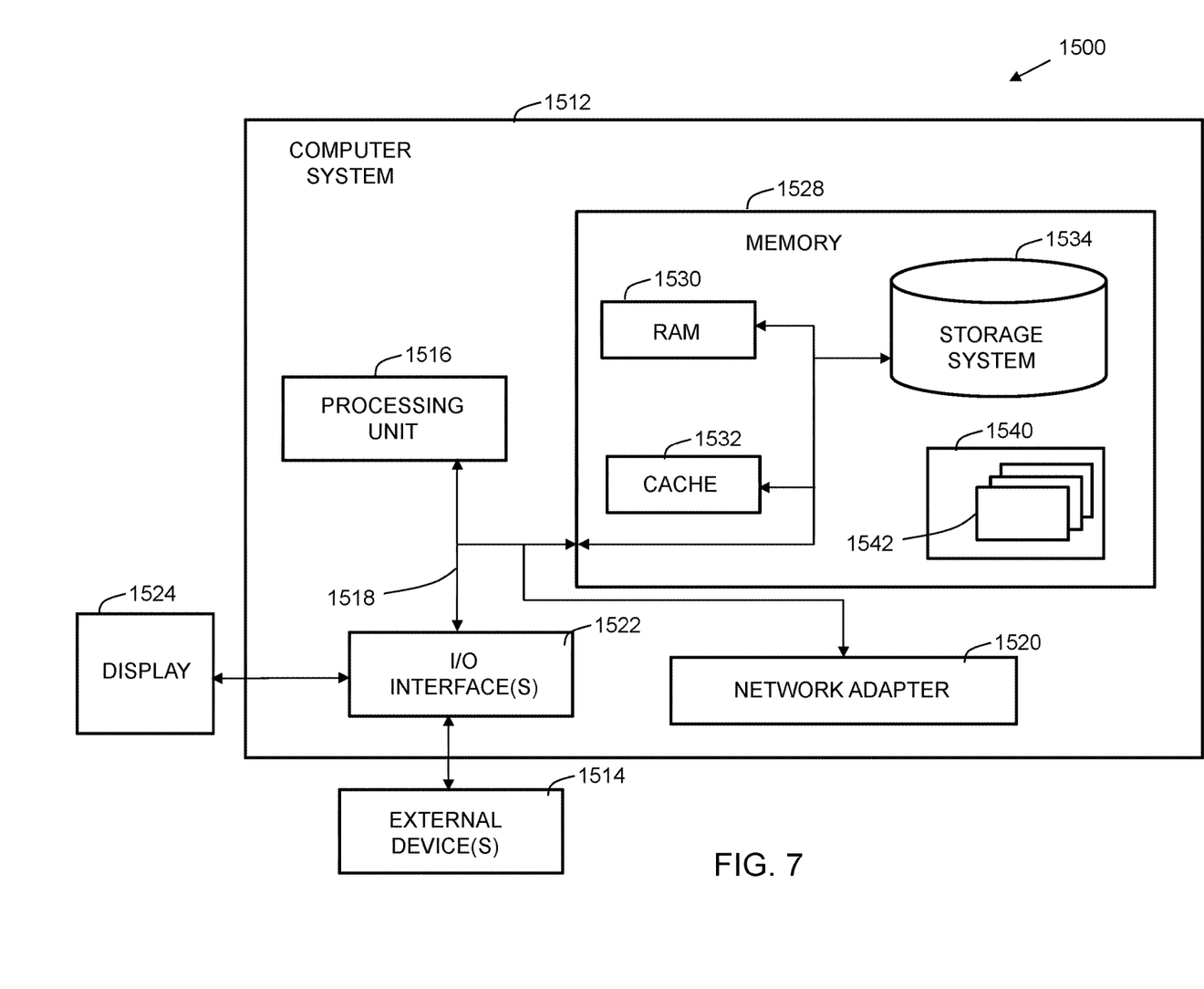
FIG. 7 shows additional details of an embodiment of the present invention.

Referring now to FIG. 7, a computerized implementation 1500 of an embodiment for dynamic injection of medical training scenarios into a surgical simulation system based on patient similarity cohort identification is described in further detail. Computerized implementation 1500 is only one example of a suitable implementation and is not intended to suggest any limitation as to the scope of use or functionality of embodiments of the invention described herein. Regardless, computerized implementation 1500 is capable of being implemented and/or performing any of the functionality set forth hereinabove.

In computerized implementation 1500, there is a computer system 1512. Examples of well-known computing systems, environments, and/or configurations that may be suitable for use with computer system 1512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

This is intended to demonstrate, among other things, that the present invention could be implemented within a network environment (e.g., the Internet, a wide area network (WAN), a local area network (LAN), a virtual private network (VPN), etc.), a cloud computing environment, a cellular network, or on a stand-alone computer system. Communication throughout the network can occur via any combination of various types of communication links. For example, the communication links can comprise addressable connections that may utilize any combination of wired and/or wireless transmission methods. Where communications occur via the Internet, connectivity could be provided by conventional TCP/IP sockets-based protocol, and an Internet service provider could be used to establish connectivity to the Internet. Still yet, computer system 1512 is intended to demonstrate that some or all of the components of implementation 1500 could be deployed, managed, serviced, etc., by a service provider who offers to implement, deploy, and/or perform the functions of the present invention for others.

Computer system 1512 is intended to represent any type of computer system that may be implemented in deploying/realizing the teachings recited herein. Computer system 1512 may be described in the general context of computer system executable instructions, such as program modules, being executed by a computer system. Generally, program modules may include routines, programs, objects, components, logic, data structures, and so on, that perform particular tasks or implement particular abstract data types. In this particular example, computer system 1512 represents an illustrative system for gathering time-annotated web interaction and biometric sensor data of web page users to extrapolate emotional responses to a web page and generating an aggregated emotional map indicative of the emotional responses. It should be understood that any other computers implemented under the present invention may have different components/software, but can perform similar functions.

Computer system 1512 in computerized implementation 1500 is shown in the form of a general-purpose computing device. The components of computer system 1512 may include, but are not limited to, one or more processors (processing units) 1516, a system memory 1528, and a bus 1518 that couples various system components including system memory 1528 to processor 1516.

Bus 1518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Processing unit 1516 refers, generally, to any apparatus that performs logic operations, computational tasks, control functions, etc. A processor may include one or more subsystems, components, and/or other processors. A processor will typically include various logic components that operate using a clock signal to latch data, advance logic states, synchronize computations and logic operations, and/or provide other timing functions. During operation, processing unit 1516 collects and routes signals representing inputs and outputs between external devices 1514 and input devices (not shown). The signals can be transmitted over a LAN and/or a WAN (e.g., T1, T3, 56 kb, X.25), broadband connections (ISDN, Frame Relay, ATM), wireless links (802.11, Bluetooth, etc.), and so on. In some embodiments, the signals may be encrypted using, for example, trusted key-pair encryption. Different systems may transmit information using different communication pathways, such as Ethernet or wireless networks, direct serial or parallel connections, USB, Firewire®, Bluetooth®, or other proprietary interfaces. (Firewire is a registered trademark of Apple Computer, Inc. Bluetooth is a registered trademark of Bluetooth Special Interest Group (SIG)).

In general, processing unit 1516 executes computer program code, such as program code for gathering time-annotated web interaction and biometric sensor data of web page users to extrapolate emotional responses to a web page and generating an aggregated emotional map indicative of the emotional responses, which is stored in memory 1528, storage system 1534, and/or program/utility 1540. While executing computer program code, processing unit 1516 can read and/or write data to/from memory 1528, storage system 1534, and program/utility 1540.

Computer system 1512 typically includes a variety of computer system readable media. Such media may be any available media that is accessible by computer system 1512, and it includes both volatile and non-volatile media, removable and non-removable media.

System memory 1528 can include computer system readable media in the form of volatile memory, such as random access memory (RAM) 1530 and/or cache memory 1532. Computer system 1512 may further include other removable/non-removable, volatile/non-volatile computer system storage media, (e.g., DVRs, RAID arrays, USB hard drives, optical disk recorders, flash storage devices, and/or any other data processing and storage elements for storing and/or processing data). By way of example only, storage system 1534 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM, or other optical media can be provided. In such instances, each can be connected to bus 1518 by one or more data media interfaces. As will be further depicted and described below, memory 1528 may include at least one program product having a set (e.g., at least one) of program modules that are configured to carry out the functions of embodiments of the invention. Program code embodied on a computer readable medium may be transmitted using any appropriate medium including, but not limited to, wireless, wireline, optical fiber cable, radio-frequency (RF), etc., or any suitable combination of the foregoing.

Program/utility 1540, having a set (at least one) of program modules 1542, may be stored in memory 1528 by way of example, and not limitation. Memory 1528 may also have an operating system, one or more application programs, other program modules, and program data. Each of the operating system, one or more application programs, other program modules, and program data or some combination thereof, may include an implementation of a networking environment. Program modules 1542 generally carry out the functions and/or methodologies of embodiments of the invention as described herein.

Computer system 1512 may also communicate with one or more external devices 1514 such as a keyboard, a pointing device, a display 1524, etc.; one or more devices that enable a consumer to interact with computer system 1512; and/or any devices (e.g., network card, modem, etc.) that enable computer system 1512 to communicate with one or more other computing devices. Such communication can occur via I/O interfaces 1522. Still yet, computer system 1512 can communicate with one or more networks such as a local area network (LAN), a general wide area network (WAN), and/or a public network (e.g., the Internet) via network adapter 1520. As depicted, network adapter 1520 communicates with the other components of computer system 1512 via bus 1518. It should be understood that although not shown, other hardware and/or software components could be used in conjunction with computer system 1512. Examples include, but are not limited to: microcode, device drivers, redundant processing units, external disk drive arrays, RAID systems, tape drives, and data archival storage systems, etc.

As can now be appreciated, disclosed embodiments provide improvements in the technical field of surgical simulation and medical training scenario generation. Embodiments provide a computer-implemented technique for selection of surgical simulation scenarios based on patient similarity cohort identification. Cohort identification may be based primarily on abnormal values (outside of an average range, e.g. outside of a three sigma standard deviation) rather than normal values (within an average range, e.g. within a three sigma standard deviation). As an example, higher glucose values (outside of an average range) may be considered as the factor for identification of a particular individual to be within a cohort, as opposed to using an individual with normal values mapped to a cohort of individuals with normal reading. Cohort identification may use Neighborhood-based and/or Distance-based algorithms to identify other people similar to the particular patient. Then, various possible outcomes are predicted. The predicted outcomes may be further narrowed based on the statistical information/confidence levels pertaining to the particular patient candidate. This information may also be used in building a 3D model (workpiece) that can be used for training. In particular, identifying a patient cohort for a patient candidate, and applying information from the cohort into the fabrication of a 3D workpiece for training can provide a medical simulation environment that more accurately represents conditions of the patient candidate than if the patient cohort information is not considered during fabrication of a 3D workpiece. As in the previously stated example, in certain segments of the population, there can exist an elevated probability of an unusual nerve placement. In other segments of the population, the unusual nerve placement may be exceedingly rare. Thus, with embodiments of the present invention, resources are devoted to simulation of the unusual nerve placement through 3D printed workpieces when the patient cohort indicates an elevated probability of occurrence, while not requiring time and resources in cases where the nerve placement is exceedingly rare. Thus, embodiments of the present invention improve the technical field of medical simulation by efficiently utilizing time and simulation resources towards situations with an elevated probability of occurrence. By rehearsing potential emergencies that can arise during a surgical procedure, the medical team is better equipped to achieve a successful outcome for the patient, and reduce associated medical costs, lowering the overall costs of healthcare.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The term "set" is intended to mean a quantity of at least one. It will be further understood that the terms "comprises" and/or "comprising", or "includes" and/or "including", or "has" and/or "having", when used in this specification, specify the presence of stated features, regions, integers, steps, operations, elements, and/or components, but do not preclude the presence or addition of one or more other features, regions, or elements.

Some of the functional components described in this specification have been labeled as systems or units in order to more particularly emphasize their implementation independence. For example, a system or unit may be implemented as a hardware circuit comprising custom VLSI circuits or gate arrays, off-the-shelf semiconductors such as logic chips, transistors, or other discrete components. A system or unit may also be implemented in programmable hardware devices such as field programmable gate arrays, programmable array logic, programmable logic devices, or the like. A system or unit may also be implemented in software for execution by various types of processors. A system or unit or component of executable code may, for instance, comprise one or more physical or logical blocks of computer instructions, which may, for instance, be organized as an object, procedure, or function. Nevertheless, the executables of an identified system or unit need not be physically located together, but may comprise disparate instructions stored in different locations which, when joined logically together, comprise the system or unit and achieve the stated purpose for the system or unit.

Further, a system or unit of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices and disparate memory devices.

Furthermore, systems/units may also be implemented as a combination of software and one or more hardware devices. For instance, location determination and alert message and/or coupon rendering may be embodied in the combination of a software executable code stored on a memory medium (e.g., memory storage device). In a further example, a system or unit may be the combination of a processor that operates on a set of operational data.

As noted above, some of the embodiments may be embodied in hardware.

The hardware may be referenced as a hardware element. In general, a hardware element may refer to any hardware structures arranged to perform certain operations. In one embodiment, for example, the hardware elements may include any analog or digital electrical or electronic elements fabricated on a substrate. The fabrication may be performed using silicon-based integrated circuit (IC) techniques, such as complementary metal oxide semiconductor (CMOS), bipolar, and bipolar CMOS (BiCMOS) techniques, for example. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor devices, chips, microchips, chip sets, and so forth. However, the embodiments are not limited in this context.

Also noted above, some embodiments may be embodied in software. The software may be referenced as a software element. In general, a software element may refer to any software structures arranged to perform certain operations. In one embodiment, for example, the software elements may include program instructions and/or data adapted for execution by a hardware element, such as a processor. Program instructions may include an organized list of commands comprising words, values, or symbols arranged in a predetermined syntax that, when executed, may cause a processor to perform a corresponding set of operations.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, may be non-transitory, and thus is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Program data may also be received via the network adapter or network interface.

Computer readable program instructions for carrying out operations of embodiments of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of embodiments of the present invention.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

While the disclosure outlines exemplary embodiments, it will be appreciated that variations and modifications will occur to those skilled in the art. For example, although the illustrative embodiments are described herein as a series of acts or events, it will be appreciated that the present invention is not limited by the illustrated ordering of such acts or events unless specifically stated. Some acts may occur in different orders and/or concurrently with other acts or events apart from those illustrated and/or described herein, in accordance with the invention. In addition, not all illustrated steps may be required to implement a methodology in accordance with embodiments of the present invention. Furthermore, the methods according to embodiments of the present invention may be implemented in association with the formation and/or processing of structures illustrated and described herein as well as in association with other structures not illustrated. Moreover, in particular regard to the various functions performed by the above described components (assemblies, devices, circuits, etc.), the terms used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of embodiments of the invention may have been disclosed with respect to only one of several embodiments, such feature may be combined with one or more features of the other embodiments as may be desired and advantageous for any given or particular application. Therefore, it is to be understood that the appended claims are intended to cover all such modifications and changes that fall within the true spirit of embodiments of the invention.

What is claimed is:

1. An electronic computation device comprising:
a processor;
a memory coupled to the processor, the memory containing instructions, that when executed by the processor, perform the process of:
retrieving a medical information record for a patient from a patient medical database;
receiving a procedure request for a patient;
identifying, by a machine learning system, a cohort for the patient based on the medical information record;
identifying, by the machine learning system, a cohort risk factor that is related to the procedure request based on the identified cohort;
determining a probability of occurrence for the cohort risk factor; and automatically altering a surgical simulation corresponding to the procedure request to include an occurrence of the cohort risk factor in response to a probability of occurrence exceeding a predetermined threshold;

executing a surgical simulation scenario that performs an interactive simulation of the procedure that is adapted to the patient by including the altered surgical simulation, wherein the surgical simulation scenario is performed by a medical professional in preparation for the procedure;

updating the patient medical database with an outcome of a real-world surgery corresponding to the procedure request; and incorporating the outcome into future identifications by the machine learning system, wherein the memory further comprises instructions, that when executed by the processor, perform the process of:

making a customized workplace in which the surgical simulation scenario is performed using a 3D printing process; and altering the surgical simulation by generating a physical element of the customized workplace that has characteristics that are specific to the identified cohort by controlling the 3D printing process using parameters pertaining to the characteristics.

2. The electronic computation device of claim 1, wherein the memory further comprises instructions, that when executed by the processor, perform the process of receiving genotypic information.

3. The electronic computation device of claim 1, wherein the memory further comprises instructions, that when executed by the processor, perform the process of receiving physiological information.

4. The electronic computation device of claim 1, wherein the memory further comprises instructions, that when executed by the processor, perform the process of identifying a cohort utilizing a Random Forest process.

5. The electronic computation device of claim 1, wherein the memory further comprises instructions, that when executed by the processor, perform the process of identifying a cohort utilizing a geographic correlation technique.

6. The electronic computation device of claim 1, wherein the memory further comprises instructions, that when executed by the processor, perform the process of:

determining a severity for the cohort risk factor; and altering the surgical simulation corresponding to the procedure request in response to a severity exceeding a predetermined level.

7. A computer program product for an electronic computation device comprising a computer readable storage medium having program instructions embodied therewith, the program instructions executable by a processor to cause the electronic computation device to perform the process of:

retrieving a medical information record for a patient from a patient medical database;

retrieving a procedure request for a patient;

identifying, by a machine learning system, a cohort for the patient based on the medical information record;

identifying, by the machine learning system, a cohort risk factor that is related to the procedure request based on the identified cohort;

determining a probability of occurrence for the cohort risk factor; and automatically altering a surgical simulation corresponding to the procedure request to include an occurrence of the cohort risk factor in response to a probability of occurrence exceeding a predetermined threshold;

executing a surgical simulation scenario that performs an interactive simulation of the procedure that is adapted to the patient by including the altered surgical simulation, wherein the surgical simulation scenario is performed by a medical professional in preparation for the procedure;

updating the patient medical database with an outcome of a real-world surgery corresponding to the procedure request; and incorporating the outcome into future identifications by the machine learning system, wherein the computer readable storage medium includes program instructions executable by the processor to cause the electronic computation device to perform the process of altering the surgical simulation by controlling a 3D printing process, comprising steps of:

making a customized workplace in which the surgical simulation scenario is performed using a 3D printing process; and altering the surgical simulation by generating a physical element of the customized workplace that has characteristics that are specific to the identified cohort by controlling the 3D printing process using parameters pertaining to the characteristics.

8. The computer program product of claim 7, wherein the computer readable storage medium includes program instructions executable by the processor to cause the electronic computation device to perform the process of:

determining the severity for the cohort risk factor; and altering a surgical simulation corresponding to the procedure request in response to a severity exceeding a predetermined level.

9. The computer program product of claim 7, wherein the computer readable storage medium includes program instructions executable by the processor to cause the electronic computation device to perform the process of identifying a cohort utilizing a geographic correlation technique.

10. The computer program product of claim 7, wherein the computer readable storage medium includes program instructions executable by the processor to cause the electronic computation device to perform the process of altering the surgical simulation by requesting an organ failure scenario.

* * * * *